(12) United States Patent
Duval

(10) Patent No.: US 8,234,940 B2
(45) Date of Patent: Aug. 7, 2012

(54) TRACE EVIDENCE COLLECTION METHOD

(76) Inventor: Joelle N. Duval, Bronx, NY (US)

( * ) Notice: Subject to any disclaimer, the term of this patent is extended or adjusted under 35 U.S.C. 154(b) by 467 days.

(21) Appl. No.: 11/941,641

(22) Filed: Nov. 16, 2007

(65) Prior Publication Data

US 2008/0115595 A1    May 22, 2008

Related U.S. Application Data

(60) Provisional application No. 60/859,888, filed on Nov. 20, 2006.

(51) Int. Cl.
*G01N 1/04* (2006.01)
(52) U.S. Cl. .................................. 73/864.71
(58) Field of Classification Search ............. 73/864.71
See application file for complete search history.

(56) References Cited

U.S. PATENT DOCUMENTS

| | | | |
|---|---|---|---|
| 4,805,468 A | 2/1989 | Choudhry | |
| 4,847,596 A * | 7/1989 | Jacobson et al. | 340/550 |
| 5,662,758 A | 9/1997 | Hamilton et al. | |
| 5,871,607 A | 2/1999 | Hamilton et al. | |
| 5,965,235 A | 10/1999 | McGuire et al. | |
| 5,968,633 A | 10/1999 | Hamilton et al. | |
| 6,099,940 A | 8/2000 | Hamilton et al. | |
| 6,193,918 B1 | 2/2001 | McGuire et al. | |
| 6,194,062 B1 | 2/2001 | Hamilton et al. | |
| 6,254,965 B1 | 7/2001 | McGuire et al. | |
| 6,260,885 B1 | 7/2001 | Massimo, Sr. | |
| 6,421,052 B1 | 7/2002 | McGuire | |
| 6,489,022 B1 | 12/2002 | Hamilton et al. | |
| 6,602,454 B2 | 8/2003 | McGuire et al. | |
| 6,602,580 B1 | 8/2003 | Hamilton et al. | |
| 6,773,647 B2 | 8/2004 | McGuire et al. | |
| 6,818,292 B2 | 11/2004 | Hamilton et al. | |
| 6,858,285 B1 | 2/2005 | Hamilton et al. | |
| 6,880,948 B2 * | 4/2005 | Koch et al. | 362/600 |
| 6,925,896 B1 | 8/2005 | Morton | |
| 2006/0130598 A1 | 6/2006 | Driessche | |
| 2007/0084100 A1 * | 4/2007 | DeLong | 40/776 |

FOREIGN PATENT DOCUMENTS

| | | | |
|---|---|---|---|
| BE | 839137 | * | 7/1976 |
| WO | 2006038023 A1 | | 4/2006 |

OTHER PUBLICATIONS

Glad Press'n Seal—1000 Uses, website (1 page); printed Nov. 16, 2007: http://1000uses.com/.

* cited by examiner

*Primary Examiner* — Robert R Raevis
(74) *Attorney, Agent, or Firm* — Patent Authority LLC; Elliot Furman

(57) ABSTRACT

A method of collecting trace evidence comprises utilizing a sheet material to recover trace evidence wherein the sheet material comprises a sheet of non-porous material having a first side and a second side, the first side comprising an active side exhibiting an adhesion peel force after activation by a user which is greater than an adhesion peel force exhibited prior to activation by a user and which is sufficient to form a continuous seal against any target surface. The adhesion peel force before activation is substantially zero. The activation of the active side requires no removal of components of the sheet of material. The sheet of material is sufficiently flexible to conform readily to any desired surface and has sufficiently small resiliency that it does not exert undue restorative forces which would tend to cause the sheet of material to break contact with such a desired surface. The method further comprises releasing the trace evidence, regardless of the type of trace evidence, from the sheet material without damaging the trace evidence and without utilizing chemicals.

9 Claims, 2 Drawing Sheets

TRACE EVIDENCE COLLECTION METHOD

This application claims the benefit of U.S. Provisional Application No. 60/859,888, filed Nov. 20, 2006, which is hereby incorporated by reference.

BACKGROUND

Trace evidence is used by forensic experts to investigate crime and accident scenes. Trace evidence can be used to indicate the direction that an investigation should take, to aid in reconstructing events, and as direct or circumstantial evidence. Thus, the proper and efficient collection and analysis of trace evidence is critical. Trace evidence may include, but is not limited to, particles large and small such as hair, paint, glass, fibers, dusts, residues, dirt, rock, as well as objects whether manmade or natural.

Tape lifting is one of the most common ways to collect trace evidence. Clear adhesive tape is selectively applied to a surface containing or potentially containing trace evidence. The evidence sticks to the tape and a clear barrier such as plastic or glass is applied to the tape to protect the evidence.

Unfortunately, tape and tape lifting have many disadvantages and problems associated with it. Tapes tend to be very sticky and therefore cannot be used on surfaces where they cannot be easily removed, such as on paper and other easily damaged or delicate surfaces. Tape will also readily collect a significant amount of non-trace evidence fibers along with trace evidence, for example unwanted clothing fibers along with trace evidence hair on the fabric. Also, tape can easily stick to itself ruining potential evidence and wasting tape. And because tape comprises a continuous adhesive sheet that sticks on a constant basis and is always exposed, contamination is possible during collection as dusts, fibers, and other matter in the air will quickly and easily stick to the tape. This remains the case even for low tack tapes that use weaker adhesives.

Thus, many things brought within proximity to the tape will stick to it, whether desirable or not. Also due to the continuous adhesive sheet the sticky side of the tape must be protected with a liner. The liner may be the plastic back of another piece of tape (as in a roll) or a separate discrete liner that is removed and discarded prior to use.

Furthermore, due to the thickness of tape, that is the combined thickness of the substrate and glue of the tape, tape does not mold well to irregularly shaped, textured, or contoured surfaces. And, because of contamination and the potentially destructive nature of tape on delicate surfaces, it cannot be indiscriminately applied to large areas. This can result in missing important trace evidence, especially on surfaces where the trace evidence easily blends in with the surface and in areas that are dark or difficult to see.

Another major problem associated with tape is the removal of the material on the tape after collection for analysis. More often than not, material cannot be simply lifted off the tape; the tape adhesive is too strong and the material will become damaged if lifting is attempted. So, solvents must be used to dissolve the adhesive and release the material. This messy procedure can damage certain type of materials. Additionally, if the trace evidence stuck to the tape displays a pattern, such as in a shoeprint, that pattern is destroyed when the solvent dissolves the adhesive.

Thus, a need presently exists for an improved trace evidence collection method.

SUMMARY

A method of collecting trace evidence comprises utilizing a sheet material to recover trace evidence wherein the sheet material comprises a sheet of non-porous material having a first side and a second side, the first side comprising an active side exhibiting an adhesion peel force after activation by a user which is greater than an adhesion peel force exhibited prior to activation by a user and which is sufficient to form a continuous seal against any target surface. The adhesion peel force before activation is substantially zero. The activation of the active side requires no removal of components of the sheet of material. The sheet of material is sufficiently flexible to conform readily to any desired surface and has sufficiently small resiliency that it does not exert undue restorative forces which would tend to cause the sheet of material to break contact with such a desired surface. The method further comprises releasing the trace evidence, regardless of the type of trace evidence, from the sheet material without damaging the trace evidence and without utilizing chemicals.

DETAILED DESCRIPTION

A sheet material which will be disclosed below is pressed onto a surface containing or potentially containing trace evidence, and removed from the surface. The trace evidence adheres to the sheet material without experiencing any of the problems or limitations of the prior art.

Figure 1:
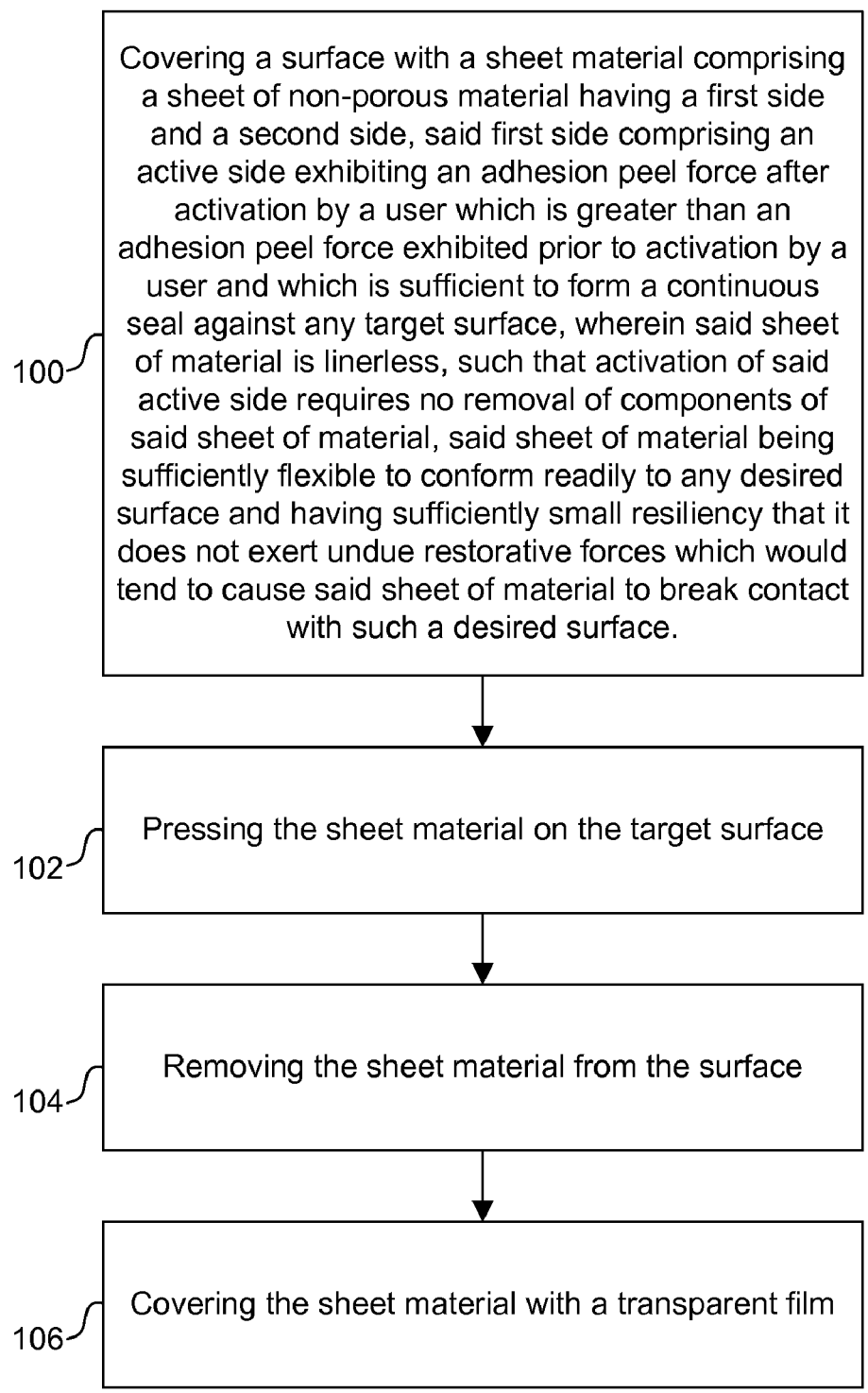
FIG. 1 shows a method for collecting trace evidence.

FIG. 1 shows a method for collecting trace evidence. A surface is covered with the sheet material disclosed in detail below (step 100), and the sheet material is pressed onto the target surface so that sheet material smoothly covers it (step 102). This is typically done by hand. The sheet material is removed from the surface (step 104). Trace evidence that was present on the surface is lifted from the surface and stuck to the sheet material. Trace evidence, or any other matter, will not stick to the sheet material unless the sheet material is activated by pressure from the pressing. This remains the case even if the sheet material is placed on top of the surface but no pressure is applied; pressure must be applied. Additionally, the sheet material can be selectively activated such that one portion of the material will stick, while another portion will not; only those areas of the sheet material to which pressure is applied will exhibit an adhesive property.

To protect the trace evidence, the sheet material is covered (step 106) with, for example, a clear transparency film. One method of covering the sheet material is to remove it completely from the surface, place the sheet material on the film or the film on the sheet material, and press the two together. Another method of covering the material is to gradually remove the material from the surface while sliding the film under between the surface and the material. Then, pressure is applied to adhere the film to the material. The film may be removed from the sheet material to expose the trace evidence for analysis or removal simply by peeling the sheet material from the film, and without the utilizing chemicals.

Figure 2:
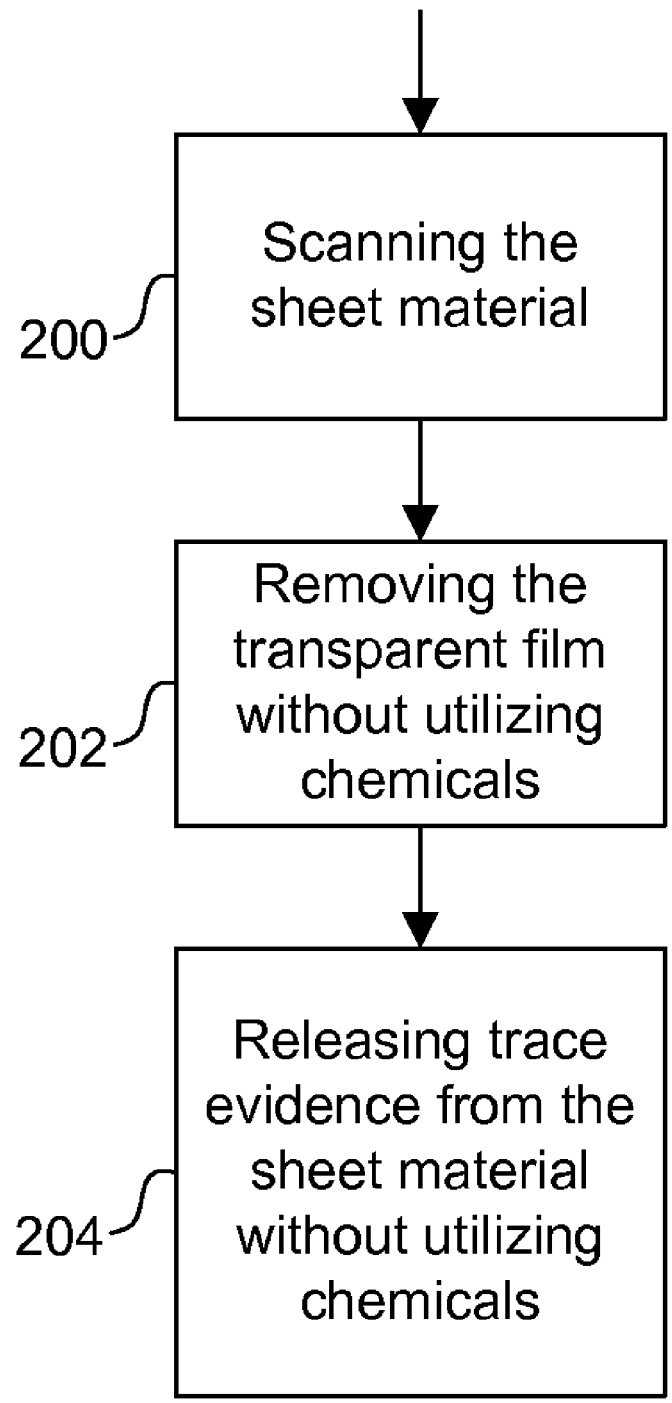
FIG. 2 shows a method for releasing trace evidence after collection.

FIG. 2 shows a method for releasing trace evidence after is collected. The sheet material may be scanned (step 200). Alternatively or in addition, the trace evidence may be released completely undamaged from the sheet material simply by removing the transparency film, if present, without utilizing chemicals (step 202) and lifting it off of the material, without utilizing chemicals (step 204). Any type of trace evidence, even extremely delicate trace evidence such as a dried leaf or paint chips, can be removed without damage and without the use chemicals. Trace evidence may be removed by hand or with forceps or tweezers. The remaining trace evidence remains intact and undisturbed. The remaining trace evidence is available to be re-visited, if necessary or desired.

The sheet material may be utilized in accordance with FIGS. 1 and 2 on many different surfaces and to collect and release a variety of trace evidence heretofore not collectible with prior art tape. For example, the sheet material is easily molded over irregularly shaped object such as the sole of a shoe, including between the shoe treads. Trace evidence collection is effective on uneven, textured, or irregularly contoured surfaces. The sheet material may be applied in large sheets over large areas to blanket an area. The sheet material when applied to grass collects loose grass, fibers, objects such as plastic, glass, plastic, and other trace evidence buried in the grass. In one experiment, when the method of FIG. 1 was carried out fibers, hair, and grass were collected along with surprisingly large objects such as clay and a pen cap.

Additionally, the sheet material when applied in the manner of FIG. 1 to delicate items such as paper does not damage the paper but collects the trace evidence on the paper. Larger trace evidence such as pieces of ceramic, clay, rocks, plastic object, and the like can be collected off of any surface along with microscopic trace evidence. Furthermore, the methods of FIGS. 1 and 2 maintain any visual patterns, such as shoe imprints or relative locations of trace evidence, while collecting the trace evidence or releasing the trace evidence.

The sheet material utilized as described above comprises a sheet of non-porous material having a first side and a second side, the first side comprising an active side exhibiting an adhesion peel force after activation by a user which is greater than an adhesion peel force exhibited prior to activation by a user and which is sufficient to form a continuous seal against any target surface, wherein the sheet of material is linerless, such that activation of the active side requires no removal of components of the sheet of material, the sheet of material being sufficiently flexible to conform readily to any desired surface and having sufficiently small resiliency that it does not exert undue restorative forces which would tend to cause the sheet of material to break contact with such a desired surface. The active side of the sheet material may further comprise a plurality of three-dimensional non-adherent protrusions extending outwardly from the sheet of material and a pressure-sensitive adhesive surrounding the non-adherent protrusions, the adhesive having a thickness less than the height of the non-adherent protrusions before activation.

Briefly, the three-dimensional non-adherent protrusion serve as standoffs such that the adhesive does not come into contact with an object (such as trace evidence) if the sheet material and object come into contact. When pressure is applied to the sheet material, the protrusions are deformed and a seal is made between the adhesive of the sheet material and object. Thus, the sheet material has substantially no adhesion properties prior to activation (that is, before pressure is applied to the sheet material). The sheet material may also be clingless.

The following patents disclose how to make such a sheet material and are hereby incorporated by reference in their entireties: U.S. Pat. Nos. 5,662,758; 5,871,607; 5,965,235; 6,193,918; 6,194,062; 6,421,052; and 6,489,022. The following related patents are also hereby incorporated by reference in their entireties: U.S. Pat. Nos. 5,968,633; 6,099,940; 6,254,965; 6,602,454; 6,602,580; 6,773,647; 6,818,292; and 6,858,285.

One example of a sheet material as disclosed herein is the plastic sealing wrap product sold under the trademark PRESS'N SEAL and under the trademark GRIPTEX. PRESS'N SEAL is a registered trademark of The Glad Products Company. GRIPTEX is a registered trademark of The Procter & Gamble Company.

The foregoing detailed description has discussed only a few of the many forms that this invention can take. It is intended that the foregoing detailed description be understood as an illustration of selected forms that the invention can take and not as a definition of the invention. It is only the following claims, including all equivalents, that are intended to define the scope of the invention.

What is claimed is:

1. A method of collecting trace evidence comprising:
    utilizing a sheet material to recover trace evidence wherein the sheet material comprises a sheet of material having a first side and a second side, the first side comprising an active side exhibiting an adhesion peel force after activation by a user which is greater than an adhesion peel force exhibited prior to activation by a user and which is sufficient to adhere to a target surface, wherein activation of the active side requires no removal of components of the sheet of material, the sheet of material being sufficiently flexible to conform readily to a desired surface and having sufficiently small resiliency that it does not exert undue restorative forces which would tend to cause the sheet of material to break contact with such a desired surface; and
    releasing the trace evidence from the sheet material without damaging the trace evidence and without utilizing chemicals.

2. The method of claim 1 wherein the sheet of material is non-porous.

3. The method of claim 1 wherein the sheet material is pressure sensitive.

4. The method of claim 1 wherein the sheet material is clingless.

5. A method of collecting trace evidence comprising:
    utilizing a sheet material to recover trace evidence wherein the sheet material comprises a sheet of material having a first side and a second side, the first side comprising an active side exhibiting an adhesion peel force after activation by a user which is greater than an adhesion peel force exhibited prior to activation by a user and which is sufficient to adhere to a target surface, wherein activation of the active side requires no removal of components of the sheet of material, the sheet of material being sufficiently flexible to conform readily to a desired surface and having sufficiently small resiliency that it does not exert undue restorative forces which would tend to cause the sheet of material to break contact with such a desired surface; and
    preserving a visual pattern indicated by the trace evidence; and
    releasing the trace evidence from the sheet material without damaging the trace evidence and without utilizing chemicals.

6. A method of collecting trace evidence comprising:
    covering a surface with a sheet material comprising a sheet of material having a first side and a second side, said first side comprising an active side exhibiting an adhesion peel force after activation by a user which is greater than an adhesion peel force exhibited prior to activation by a user and which is sufficient to adhere to a target surface, wherein said sheet of material is linerless, such that activation of said active side requires no removal of components of said sheet of material, said sheet of material being sufficiently flexible to conform readily to a desired surface and having sufficiently small resiliency that it does not exert undue restorative forces which would tend to cause said sheet of material to break contact with such a desired surface;
pressing the sheet material on the target surface;
removing the sheet material from the surface;
wherein trace evidence adheres to the sheet material; and
releasing trace evidence from the sheet material without damaging the trace evidence and without utilizing chemicals.

7. A method of collecting trace evidence comprising:
covering a surface with a sheet material comprising a sheet of material having a first side and a second side, said first side comprising an active side exhibiting an adhesion peel force after activation by a user which is greater than an adhesion peel force exhibited prior to activation by a user and which is sufficient to adhere to a target surface, wherein said sheet of material is linerless, such that activation of said active side requires no removal of components of said sheet of material, said sheet of material being sufficiently flexible to conform readily to a desired surface and having sufficiently small resiliency that it does not exert undue restorative forces which would tend to cause said sheet of material to break contact with such a desired surface;
pressing the sheet material on the target surface;
removing the sheet material from the surface;
wherein trace evidence adheres to the sheet material;
covering the sheet material with a transparent film; and
removing the transparent film.

8. A method of collecting trace evidence comprising:
covering a surface with a sheet material comprising a sheet of material having a first side and a second side, said first side comprising an active side exhibiting an adhesion peel force after activation by a user which is greater than an adhesion peel force exhibited prior to activation by a user and which is sufficient to adhere to a target surface, wherein said sheet of material is linerless, such that activation of said active side requires no removal of components of said sheet of material, said sheet of material being sufficiently flexible to conform readily to a desired surface and having sufficiently small resiliency that it does not exert undue restorative forces which would tend to cause said sheet of material to break contact with such a desired surface;
pressing the sheet material on the target surface;
removing the sheet material from the surface;
wherein trace evidence adheres to the sheet material;
covering the sheet material with a transparent film;
removing the transparent film; and
analyzing the trace evidence.

9. A method of collecting trace evidence comprising:
covering a surface with a sheet material comprising a sheet of material having a first side and a second side, said first side comprising an active side exhibiting an adhesion peel force after activation by a user which is greater than an adhesion peel force exhibited prior to activation by a user and which is sufficient to adhere to a target surface, wherein said sheet of material is linerless, such that activation of said active side requires no removal of components of said sheet of material, said sheet of material being sufficiently flexible to conform readily to a desired surface and having sufficiently small resiliency that it does not exert undue restorative forces which would tend to cause said sheet of material to break contact with such a desired surface;
pressing the sheet material on the target surface;
removing the sheet material from the surface;
wherein trace evidence adheres to the sheet material;
covering the sheet material with a transparent film; and
scanning the sheet material.

* * * * *